(12) United States Patent
Gracia Ferrer et al.

(10) Patent No.: US 6,407,108 B1
(45) Date of Patent: Jun. 18, 2002

(54) 1,2,4-TRIAZOLO(4,3-B)PYRIDO(3,2-D) PYRIDAZINE DERIVATIVES AND PHARMACEUTICAL COMPOSITIONS CONTAINING THEM

(75) Inventors: Jordi Gracia Ferrer; M$^a$ Isabel Crespo Crespo; Armando Vega Noverola; Andres Fernandez Garcia, all of Barcelona (ES)

(73) Assignee: Almirall Prodesfarma, S.A., Barcelona (ES)

( * ) Notice: Subject to any disclaimer, the term of this patent is extended or adjusted under 35 U.S.C. 154(b) by 0 days.

(21) Appl. No.: 09/496,019

(22) Filed: Jan. 28, 2000

Related U.S. Application Data

(63) Continuation of application No. PCT/EP98/04340, filed on Jul. 13, 1998.

(30) Foreign Application Priority Data

Jul. 29, 1997 (ES) ................................................ 9701670

(51) Int. Cl.$^7$ ................... A61K 31/5025; C07D 471/14
(52) U.S. Cl. ........................ 514/248; 544/234
(58) Field of Search ........................... 544/234; 514/248

(56) References Cited

U.S. PATENT DOCUMENTS 4,381,303 A  4/1983  Schmidt et al.

FOREIGN PATENT DOCUMENTS

| WO | WO 91/12251 | | 8/1991 |
|---|---|---|---|
| WO | 93/07146 | * | 4/1993 |
| WO | WO 97/03985 | | 2/1997 |

OTHER PUBLICATIONS

Fahmy et al, *Synthetic Communications* 28(15) p2871–2886, 1998.*
Nicholson et al, *TIPS*, vol. 121, p. 19–27, 1991.*
Ishii et al., Chemical Abstracts, vol. 91, No. 13326z, 1979.*
Nyman et al, Medline Abstract for Clinical and Experimental Immunology, 108(3),p. 415–419, 1997.*

* cited by examiner

Primary Examiner—Emily Bernhardt
(74) Attorney, Agent, or Firm—Venable; Marina V. Schneller

(57) ABSTRACT

Heterocyclic compounds of formula(I),

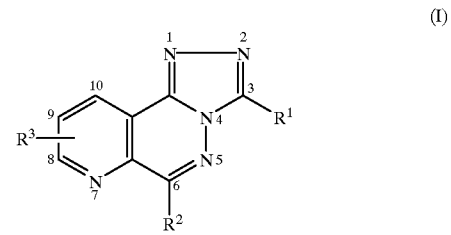

wherein $R^1$ represents a hydrogen atom or a —$(CH_2)_m$—Y group, wherein m is an integer from 0 to 4 and Y represents an alkyl, haloalkyl, alkoxy, alkoxycarbonyl, $C_3$–$C_7$ cycloalkyl, norbornyl or phenylalkenyl group, or an aromatic group which aromatic group ^ may optionally be substituted by one or more halogen atoms; $R^2$ represents an aromatic group which aromatic group may optionally be substituted by one or more halogen atoms or alkyl, alkoxy, $C_3$–$C_6$ cycloalkoxy, methylenedioxy, nitro, dialkylamino or trifluoromethyl groups, and $R^3$ represents a hydrogen or halogen atom or an alkyl group, and pharmaceutically acceptable salts thereof, processes for preparing the same are disclosed herein. The compounds are phosphodiesterase 4 inhibitors.

8 Claims, No Drawings

1,2,4-TRIAZOLO(4,3-B)PYRIDO(3,2-D) PYRIDAZINE DERIVATIVES AND PHARMACEUTICAL COMPOSITIONS CONTAINING THEM

CROSS REFERENCE TO RELATED APPLICATIONS

This application is a continuation of PCT/EP98/04340, which is relied upon under 35 U.S.C. § 120 and incorporated by reference herein.

This invention relates to new therapeutically useful heterocyclic compounds, to process for their preparation and to pharmaceutical compositions containing them.

It is known that inhibitors of phosphodiesterase 4 (PDE 4) are useful in the treatment of inflammatory and allergic processes such as asthma, non-steroidal antiinflammatory drugs-induced gastrointestinal damage and atopic dermatitis.

EP-A-85,840 discloses a series of triazolo-phthalazine derivatives of formula:

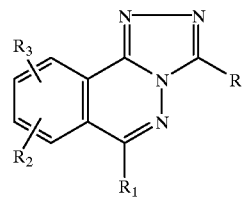

which are useful as anxiolytic agents.

We have now found that the presence of a pyridine ring instead of the benzo ring in the above structure, provides new compounds which inhibit cyclic phosphodiesterases, in particular type 4 cyclic phosphodiesterases and have a very low emetic activity (10–100 times less active than rolipram in inducing emesis in dogs).

Accordingly, the present invention provides a compound which is a heterocycle of formula (I):

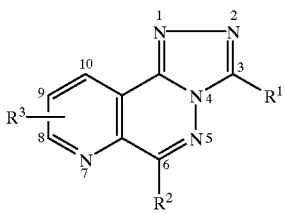

wherein:

$R^1$ represents a hydrogen atom or a —(CH$_2$)$_m$—Y group, wherein m is an integer from 0 to 4 and Y represents an alkyl, haloalkyl (preferably trifluoromethyl), alkoxy, alkoxycarbonyl, $C_3$–$C_7$ cycloalkyl, norbornyl (preferably 2-norbornyl) or phenylalkenyl group, or an aromatic group (preferably phenyl or pyridyl) which aromatic group Y may optionally be substituted by one or more halogen atoms;

$R^2$ represents an aromatic group (preferably phenyl, naphthyl or thienyl) which aromatic group may optionally be substituted by one or more halogen atoms or alkyl, alkoxy, $C_3$–$C_6$ cycloalkoxy, methylenedioxy, nitro, dialkylamino or trifluoromethyl groups; and $R^3$ represents a hydrogen or halogen atom (preferably chloro) or an alkyl group, and pharmaceutically acceptable salts thereof.

The alkyl, haloalkyl, alkenyl or alkynyl groups and moieties, such as in the alkoxy groups, mentioned in relation to the groups $R^1$–$R^3$ in compounds of the invention are usually "lower" alkyl, that is containing up to 6 and particularly up to 4 carbon atoms, the hydrocarbon chain being branched or straight. Examples of alkyl groups and moieties are CH$_3$, C$_2$H$_5$, C$_3$H$_7$, i-C$_3$H$_7$, n-C$_4$H$_9$, i-C$_4$H$_9$, isoamyl and neopentyl.

When any of the groups, such as $R^1$ or $R^2$ has a chiral centre, the compounds of formula (I) exhibit optical isomerism and the isomers are within the scope of the present invention.

Examples of $R^1$ are the preferred alkyl groups mentioned above, cyclopropyl, cyclopropylmethyl, cyclobutyl, cyclobutylmethyl, cyclopentyl and cyclopenthylmethyl.

Examples of $R^2$ are phenyl, 3-chlorophenyl, 4-chlorophenyl, 3-fluorophenyl, 4-fluorophenyl and 3-nitrophenyl.

Examples of $R^3$ are hydrogen, alkyl or chloro, preferably in the 8- or 9-positions.

The most preferred compounds of the invention are 6-(4-fluorophenyl)-3-isobutyl-1,2,4-triazolo[4,3-b]pyrido[3,2-d]pyridazine, 3-cyclopropylmethyl-6-(3-nitrophenyl)-1,2,4-triazolo[4,3-b]pyrido[3,2-d]pyridazine, 3-cyclopropyl-6-phenyl-1,2,4-triazolo[4,3-b]pyrido[3,2-d]pyridazine, and 3-cyclobutylmethyl-6-(3-nitrophenyl)-1,2,4-triazolo[4,3-b]pyrido[3,2-d]pyridazine.

According to a further feature of the present invention, the heterocyclic compounds of formula (I) can be prepared from the corresponding hydrazine derivative of formula (II)

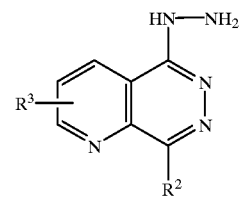

wherein $R^2$ and $R^3$ are as defined above, by reaction with a reactive derivative of a carboxylic acid of the general formula (III):

HOOC—R$^1$     (III)

wherein $R^1$ is as defined above. The reactive derivative of the said carboxylic acid may be, for example, a halide (preferably chloride), an anhydride or a mixed anhydride.

The reaction is preferably carried out in an inert organic solvent such as methylene chloride, dioxane or tetrahydrofuran, in the presence of an organic nitrogen-containing base, e.g. triethylamine and at a temperature between −10° C. and +60° C. In the reaction, the corresponding hydrazide of general formula (IV) is first formed:

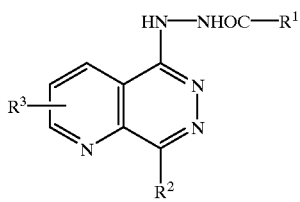

wherein $R^1$, $R^2$ and $R^3$ are as defined above. A suspension of this hydrazide (IV) in an organic solvent such as dioxane, tetrahydrofuran, isopropanol or n-butanol, is heated, for example at the boiling point of the solvent, to give the corresponding heterocyclic compound of formula (I)

The hydrazine derivative of formula (II) may be prepared by:

1) reacting a hydrazone of formula (V):

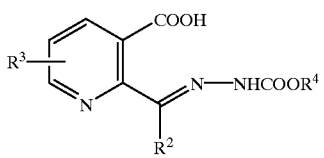

wherein $R^2$ and $R^3$ are as defined above and $R^4$ is an alkyl group, with a phosphorus halide or phosphorus oxyhalide (preferably phosphorus oxychloride), to form the intermediate compound of formula (VI):

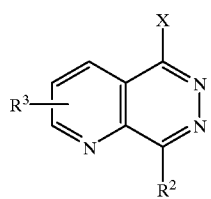

wherein $R^2$ and $R^3$ are as defined above and X is a chlorine or bromine atom;

2) reacting compound (VI) with an alkyl carbazate (preferably t-butyl carbazate) of formula (VII):

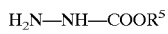

$H_2N-NH-COOR^5$ (VII)

wherein $R^5$ is an alkyl group, to give the alkoxycarbonylhydrazine derivative (VIII):

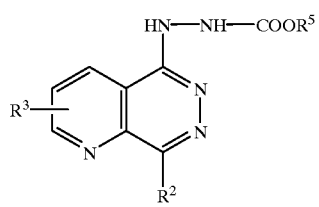

wherein $R^2$, $R^3$ and $R^5$ are as defined above; and 3) treating compound (VIII) with hydrogen chloride in an anhydrous solvent as ethanol.

The reaction between the hydrazone of formula (V) and a phosphorus halide or phosphorus oxyhalide is carried out with an excess of reagent at a temperature from 80° C. to 120° C., then removed the excess of reagent and poured into cold water. In this way the compound (VI) is obtained.

The reaction of (VI) with the alkyl carbazate of formula (VII) to obtain the corresponding alkoxycarbonylhydrazine derivative (VIII), is preferably carried out in the presence of an organic solvent as tetrahydrofuran or dioxan at a temperature of from 60° C. to the boiling point of the reaction medium.

The alkoxycarbonylhydrazine derivative (VIII) may, for example, be transformed into the hydrazine derivative (II) at room temperature in hydrogen chloride-ethanol saturated solution.

The hydrazone derivatives or formula (V) are known compounds which can be prepared from the corresponding 2-acylnicotinic acid by known methods described in the literature.

The inhibition of cyclic nucleotide phosphodiesterase 4 from guinea-pig hearts was performed using 96-well microtiter plates as described by Verghese et al., (Molecular Pharmacology, 47, 1164–1171 (1995)).

The results from such test are shown in Table 1.

TABLE 1

| Compound * | PDE4 $IC_{50}$ ($\mu$M) |
|---|---|
| A | 10 |
| 6 | 2 |
| 7 | 0.3 |
| 12 | 3 |
| 31 | 0.2 |
| 47 | 0.7 |
| 55 | 0.2 |
| 60 | 0.1 |
| 61 | 2 |
| 109 | 0.04 |
| 112 | 0.7 |
| 113 | 0.2 |

* See structures in Table 2.

Compound A is 3-isobutyl-6-phenyl-1,2,4-triazolo[3,4-a]phthalazine, a compound included in EP-A-85,340.

As it can be seen from Table 1, the compounds of formula (I) are cyclic phosphodiesterase inhibitors, in particular type 4 cyclic AMP phosphodiesterase inhibitors. The compounds are also capable of blocking the production of some pro-inflammatory cytokines such as, for example, TNFα. Thus, they can be used in the treatment of allergic, inflammatory and immunological diseases, as well as those diseases or conditions where the blockade of pro-inflammatory cytokines or the selective inhibition of PDE 4 could be of benefit.

These diseases states Include asthma, rheumatoid arthritis, osteoarthritis, osteoporosis, bone-formation disorders, glomerulonephritis, multiple sclerosis, Graves ophtalmopathy, myasthenia gravis, insulin-dependent diabetes mellitus, graft rejection, gastrointestinal disorders such as ulcerative colitis or Crohn disease, septic shock, adult distress respiratory syndrome, and skin diseases such as atopic dermatitis, contact dermatitis, acute dermatomyositis and psoriasis.

They can also be used as improvers of cerebrovascular function as well as in the treatment of other CNS related diseases such as dementia, Alzheimer's disease, depression, and as nootropic agents.

The compounds of the present invention are also of benefit when administered in combination with other drugs such as steroids and immunosuppressive agents, such as cyclosporin A, rapamycin or T-cell receptor blockers. In this case the administration of the compounds allows a reduction of the dosage of the other drugs, thus preventing the appearance of the undesired side effects associated with both steroids and immunosuppressants.

The compounds of the invention have also shown their efficacy in blocking, after preventive and/or curative treatment, the erosive and ulcerogenic effects induced by a variety of etiological agents, such as antiinflammatory drugs (steroidal or non-steroidal antiinflammatory agents), stress, ammonia, ethanol and concentrated acids. They can be used alone or in combination with antacids and/or antisecretory drugs in the preventive and/or curative treatment of gastrointestinal pathologies like drug-induced ulcers, peptic ulcers, *H. Pylori*-related ulcers, esophagitis and gastroesophageal reflux disease.

They can also be used in the treatment of pathological situations where damage to the cells or tissues is produced through conditions like anoxia or the production of an excess of free radicals. Examples of such beneficial effects are the protection of cardiac tissue after coronary artery occlusion or the prolongation of cell and tissue viability when the compounds of the invention are added to preserving solutions intended for storage of transplant organs or fluids such as blood or sperm. They are also of benefit on tissue repair and wound healing.

The present invention also provides a heterocyclic compound of formula (I) for use in a method of treatment of the human or animal body by therapy, particularly for use as a PDE 4 inhibitor or to block the production of a pro-inflammatory cytokine such as TNFα.

The present invention additionally provides a pharmaceutical composition which comprises, as active ingredient, at least one heterocyclic compound of formula (I), and a pharmaceutically acceptable carrier or diluent.

Preferably the compositions are in a form suitable for oral, inhalation, rectal, transdermal, nasal, topical or parenteral administration.

The pharmaceutically-acceotable carriers or diluents which are admixed with the active compound or compounds to form the compositions of this invention are well known per se and the actual excipients used depend inter alia on the intended method of administration of the compositions.

Compositions of this invention are preferably adaoted for administration per os. The compositions for oral administration may take the form of tablets, capsules, lozenges or effervescent granules or liquid preparations such as elixirs, syrups or suspensions, all containing-one or more compounds of the invention. Such preparations may be made by methods well known in the art, for instance by mixing the heterocyclic compound of formula (I) with the pharmaceutically acceptable carrier or diluent.

The diluents which may be used in the preparation of the compositions Include those liquid and solid diluents which are compatible with the active ingredient, together with colouring or flavouring agents if desired. Tablets or capsules may conveniently contain from 1 to 100 mg and preferably from 5 to 50 mg of active ingredient. The compounds may also be incorporated into pellets coated with appropriate natural or synthetic polymers known in the art to produce sustained release characteristics or incorporated with polymers into tablet form to produce the same characteristics.

The liquid compositions adapted for oral use may be in the form of solutions, suspensions or aerosols. The solutions may be aqueous or aqueous-alcoholic solutions in association with, for example, sucrose or sorbitol to form a syrup.

The suspensions may comprise an insoluble or microencapsulated form of an active compound of the invention in association with water and other acceptable solvents together with a suspending agent or flavouring agent.

Compositions for inhalation administration may be in the form of solutions, suspensions or micronized powder, contained in an appropriate inhaler.

Compositions for parenteral injection may be prepared, which may or may not be freeze-dried and which may be dissolved in water or an appropriate parenteral injection fluid.

In human therapy, the doses of the heterocyclic compound depend on the desired effect and duration of the treatment; adult doses are generally from 1 mg to 100 mg per day. In general the physician will decide the posology, taking Into account the age and weight of the patient being treated.

The following Examples further illustrate the invention.

EXAMPLE 1 a) A mixture of t-butoxycarbcnylhydrazone of 2-benzoylnicotinic acid (45 g; 13.2 mols) in phosphorus oxychloride (500 ml) was boiled under reflux for one hour, then the excess of phosphorus oxychloride was removed under reduced pressure, the residue treated with ice-water and extracted twice with methylene chloride. The organic solution was washed with 4% sodium bicarbonate aqueous solution, with brine and after drying ($Na_2SO_4$), the solvent removed in vacuo. The obtained solid was collected with a mixture of diethyl ether-petrol ether 1:1 to give 5-chloro-8-phenylpyrido[2,3-d]pyridazine as a red solid, (25.4 g; 80% yield).

b) To a suspension of the above compound (18.2; 0.075 mols) in anhydrous tetrahydrofuran (180 ml), t-butyl carbazate (10.0 g; 0.075 mols) was added and the mixture was boiled under reflux for one hour. After cooling the crystallized solid was collected by filtration when 5-t-butoxycarbonylhydrazino-8-phenylpyrido[2,3-d]pyridazine was obtained (28.5 g). This compound was solved in ethanol (150 ml), hydrogen chloride in ethanol saturated solution (100 ml) was added and the resulting mixture stirred at room temperature for 15 hours. A solid was formed which was collected by filtration and washed with diethyl ether to give 5-hydrazino-8-phenylpyrido[2,3-d]pyridazine dihydrochloride (21.6 g; 92% yield).

c) To a suspension of 5-hydrazino-8-phenylpyrido[2,3-d]pyridazine dihydrochloride (1.24 g; 0.004 mols) in methylene chloride (30 ml), triethylamine (1.9 ml; 0.013 mols) was added, then stirred at room temperature for 15 minutes and pivaloyl chloride (0.5 ml; 0.0044 moles) slowly added. After stirring at room temperature for two hours, water (30 ml) was added, the formed yellow solid, collected by filtration and washed with diethyl ether to give the intermediate hydrazide. This compound was suspended in n-butanol (30 ml), boiled under reflux for 15 hours and on cooling, crystallized a white solid which was collected by filtration and washed with diethyl ether. The obtained solid was purified by flash column chromatography with silica gel and methylene chloride-ethanol-ammonium hydroxide 200:8:1 as eluent. 3-t-butyl-6-phenyl-1,2,4-triazolo[-4,3-b]pyrido[3,2-d]pyridazine was obtained (0.83 g; 69% yield), m.p. 188.1 (determined by Differential Scanning Calorimetry, Perkin-Elmer DSC-7 (compound 8 in Table 2).

The heterocyclic compounds of formula (I) in Table 2 were prepared according to the processes disclosed in this Example, but with the appropriate starting materials.

TABLE 2

| Compound | R¹ | R² | R³ | m.p. ° C. |
|---|---|---|---|---|
| 1 | H | C₆H₅ | H | 215.8 |
| 2 | CH₃ | " | " | 215.9 |
| 3 | C₂H₅ | " | " | 194.1 |
| 4 | C₃H₇ | " | " | 168.1 |
| 5 | i-C₃H₇ | " | " | 176.8 |
| 6 | n-C₄H₉ | " | " | 162.9 |
| 7 | i-C₄H₉ | " | " | 179.7 |
| 8 | t-C₄H₉ | " | " | 188.1 |
| 9 | n-C₅H₁₁ | " | " | 137.4 |
| 10 | neopentyl | " | " | 216.3 |
| 11 | t-amyl | " | " | 153 |
| 12 | cyclopropyl | " | " | 244.3 |
| 13 | cyclobutyl | " | " | 218 |
| 14 | cyclopentyl | " | " | 202.4 |
| 15 | cyclohexyl | " | " | 196.3 |
| 16 | cyclopropyl-CH₂ | " | " | 195 |
| 17 | cyclobutyl-CH₂ | " | " | 183 |
| 18 | cyclopentyl-CH₂ | " | " | 193 |
| 19 | cyclohexyl-CH₂ | " | " | 212.8 |
| 20 | 2-norbornyl-CH₂ | " | " | 217 |
| 21 | C₆H₅ | " | " | 304.1 |
| 22 | C₆H₅—CH₂ | " | " | 192 |
| 23 | C₆H₅—CH₂CH₂ | " | " | 176 |
| 24 | C₆H₅—CH=CH | " | " | 278 |
| 25 | CF₃ | " | " | 192.5 |
| 26 | H₃CO—CH₂ | " | " | 159 |
| 27 | 2-ClC₆H₄ | " | " | 206 |
| 28 | 4-pyridyl | " | " | 333.4 |
| 29 | CH₃ | 4-FC₆H₄ | " | 276 |
| 30 | n-C₄H₉ | " | " | 111 |
| 31 | i-C₄H₉ | " | " | 135 |
| 32 | t-C₄H₉ | " | " | 195 |
| 33 | neopentyl | " | " | 216 |
| 34 | cyclopropyl | " | " | 245 |
| 35 | cyclohexyl | " | " | 177 |
| 36 | cyclopropyl-CH₂ | " | " | 160 |
| 37 | cyclobutyl-CH₂ | " | " | 132 |
| 38 | cyclopentyl-CH₂ | " | " | 162 |
| 39 | 2-norbornyl-CH₂ | " | " | 161 |
| 40 | C₆H₅—CH=CH | " | " | 272 |
| 41 | C₂H₅OOC—CH₂ | " | " | 185 |
| 42 | i-C₄H₉ | 3-FC₆H₄ | — | 147 |
| 43 | neopentyl | " | " | 190 |
| 44 | cyclopropyl | " | " | 222 |
| 45 | cyclopropyl-CH₂ | " | " | 174 |
| 46 | cyclobutyl-CH₂ | " | " | 139 |
| 47 | cyclopentyl-CH₂ | " | " | 145 |
| 48 | i-C₄H₉ | 2-FC₆H₄ | " | 202 |
| 49 | t-C₄H₉ | " | " | 212 |
| 50 | neopentyl | " | " | 235 |
| 51 | cyclopropyl | " | " | 262 |
| 52 | cyclopropyl-CH₂ | " | " | 224 |
| 53 | i-C₄H₉ | 4-ClC₆H₄ | — | 133 |
| 54 | cyclopropyl | " | " | 208 |
| 55 | i-C₄H₉ | 3-ClC₆H₄ | " | 113 |
| 56 | t-C₄H₉ | " | " | 160 |
| 57 | neopentyl | " | " | 177 |
| 58 | t-amyl | " | " | 150 |
| 59 | cyclopropyl | " | " | 189 |
| 60 | cyclopropyl-CH₂ | " | " | 136 |
| 61 | cyclobutyl-CH₂ | " | " | 156 |
| 62 | cyclopentyl-CH₂ | " | " | 147 |
| 63 | i-C₄H₉ | 2-ClC₆H₄ | " | 182 |
| 64 | neopentyl | " | " | 216 |
| 65 | cyclopropyl | " | " | 198 |

TABLE 2-continued

| Compound | R¹ | R² | R³ | m.p. ° C. |
|---|---|---|---|---|
| 66 | i-C₄H₉ | 4-BrC₆H₄ | " | 135 |
| 67 | neopentyl | " | " | 204 |
| 68 | cyclopropyl | " | " | 208 |
| 69 | cyclopropyl-CH₂ | " | " | 140 |
| 70 | cyclopentyl-CH₂ | " | " | 187 |
| 71 | 2-norbornyl-CH₂ | " | " | 174 |
| 72 | i-C₄H₉ | 3-BrC₆H₄ | " | 152 |
| 73 | t-C₄H₉ | " | " | 160 |
| 74 | neopentyl | " | " | 177 |
| 75 | cyclopropyl | " | " | 186 |
| 76 | cyclopentyl-CH₂ | " | " | 143 |
| 77 | i-C₄H₉ | 3,4-diClC₆H₃ | — | 143 |
| 78 | neopentyl | " | " | 215 |
| 79 | i-C₄H₉ | 3-CH₃C₆H₄ | " | 119 |
| 80 | cyclopropyl | " | " | 206 |
| 81 | i-C₄H₉ | 2-CH₃C₆H₄ | — | 147 |
| 82 | neopentyl | " | " | 191 |
| 83 | cyclopropyl | " | " | 200 |
| 84 | i-C₄H₉ | 3,4-diCH₃C₆H₃ | " | 165 |
| 85 | neopentyl | " | " | 184 |
| 86 | cyclopropyl | " | " | 182 |
| 87 | cyclohexyl | " | " | 211 |
| 88 | cyclopentyl-CH₂ | " | " | 144 |
| 89 | i-C₄H₉ | 3-CF₃C₆H₄ | " | 139 |
| 90 | cyclopropyl | " | " | 172 |
| 91 | cyclopentyl-CH₂ | " | " | 141 |
| 92 | i-C₄H₉ | 4-CH₃OC₆H₄ | " | 177 |
| 93 | cyclopropyl | " | " | 164 |
| 94 | i-C₄H₉ | 3-CH₃OC₆H₄ | " | 119 |
| 95 | neopentyl | " | " | 155 |
| 96 | cyclopropyl | " | " | 192 |
| 97 | i-C₄H₉ | 2-CH₂OC₆H₄ | " | 181 |
| 98 | cyclopropyl | " | " | 211 |
| 99 | " | 3,4-diCH₃OC₆H₃ | " | 177 |
| 100 | i-C₄H₉ | (methylenedioxy-methylphenyl) | " | 158 |
| 101 | t-C₄H₉ | " | " | 251 |
| 102 | neopentyl | " | " | 208 |
| 103 | cyclopropyl | " | " | 208 |
| 104 | i-C₄H₉ | (cyclopentyloxy-methoxy-methylphenyl) | " | 193 |
| 105 | t-C₄H₉ | " | " | 210 |
| 106 | neopentyl | " | " | 219 |
| 107 | cyclopropyl | " | " | 162 |
| 108 | i-C₃H₇ | 3-NO₂C₆H₄ | " | 176 |
| 109 | i-C₄H₉ | " | " | 178 |
| 110 | neopentyl | " | " | 229 |
| 111 | cyclopropyl | " | " | 234 |
| 112 | cyclopropyl-CH₂ | " | " | 164 |
| 113 | cyclobutyl-CH₂ | " | " | 150 |
| 114 | cyclopentyl-CH₂ | " | " | 183 |
| 115 | cyclopropyl | 3-(CH₃)₂NC₆H₄ | " | 213 |

TABLE 2-continued

| Compound | $R^1$ | $R^2$ | $R^3$ | m.p. °C. |
|---|---|---|---|---|
| 116 | i-$C_4H_9$ | 2-naphthyl | " | 140 |
| 117 | cyclopropyl | " | " | 212 |
| 118 | i-$C_4H_9$ | 2-thienyl | " | 196 |
| 119 | cyclopropyl | " | " | 214 |
| 120 | i-$C_4H_9$ | 3-thienyl | " | 166 |
| 121 | cyclopropyl | " | " | 183 |
| 122 | i-$C_4H_9$ | $C_6H_5$ | 8-$H_3C$ | 170 |
| 123 | neopentyl | " | " | 221 |
| 124 | cyclopropyl | " | " | 185 |
| 125 | cyclopentyl-$CH_2$ | " | " | 163 |
| 126 | 2-norbornyl-$CH_2$ | " | " | 193 |
| 127 | i-$C_4H_9$ | " | 9-Cl | 174 |
| 128 | cyclopropyl | " | " | 149 |
| 129 | cyclopropyl-$CH_2$ | " | " | 175 |
| 130 | cyclopentyl-$CH_2$ | " | " | 175 |

The following Examples illustrate pharmaceutical compositions according to the invention.

EXAMPLE 2

3,000 inhalation-flasks each containing 40 mg of 3-t-butyl-6-phenyl-1,2,4-triazolo[4,3-b]pyrido[3,2-d]pyridazine (active compound) were prepared as follows:

| Active compound | 120 g |
|---|---|
| Sorbitan trioleate | 4 g |
| propellent q.s. | 60 l |

Procedure

The microcrystalline suspension prepared with these ingredients was introduced in the inhalation-flasks at a volume of 20 ml per flask with a filling machine. The flasks were furnished with an appropriate valve which released 0.2 ml of suspension for each, activation (0.4 mg of active compound)

EXAMPLE 3

15,000 capsules each containing 20 mg of 3-t-butyl-6-phenyl-1,2,4-triazolo[4,3-b]pyrido[3,2-d]pyridazine (active compound) were prepared from the following formulation:

| Active compound | 300 g |
|---|---|
| Sodium carboxymethyl starch | 330 g |
| Talc | 195 g |
| Hydrogenated castor oil | 165 g |
| Corn starch | 495 g |

Procedure

The above ingredients were sieved through a 60 mesh sieve, then mixed in a suitable mixer and filled into 15,000 gelatine capsules.

What is claimed is:
1. A compound of formula (I)

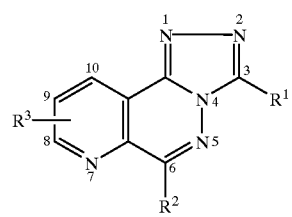

(I)

wherein;
R$^1$ represents a hydrogen atom or a —(CH$_2$)$_m$—Y group, wherein m is an integer from 0 to 4 and Y represents a C$_1$–C$_6$ alkyl, C$_1$–C$_6$ haloalkyl, C$_1$–C$_6$ alkoxy, C$_2$–C$_7$ alkoxycarbonyl, C$_3$–C$_7$, cycloalkyl, norbornyl or C$_8$–C$_{12}$ phenylalkenyl group, or a phenyl or pyridyl group which may be unsubstituted or substituted by one or more halogen atoms;
R$^2$ represents a phenyl, naphthyl or thienyl group which may be unsubstituted or substituted by one or more halogen atoms or C$_1$–C$_6$ alkyl, C$_1$–C$_6$ alkoxy, C$_1$–C$_6$ cycloalkoxy, methylenedioxy, nitro, di(C$_1$–C$_6$) alkylamino or trifluoromethyl groups; and
R$^3$ represents a hydrogen or halogen atom or a C$_1$–C$_6$ alkyl group,
and pharmaceutically acceptable salts thereof.
2. A compound according to claim 1 wherein R$^1$ represents —(CH$_2$)$_m$—Y wherein m is 0 or 1 and Y represents C$_{1-6}$ alkyl or C$_{3-7}$ cycloalkyl.
3. A compound according to claim 1 or 2 wherein R$^2$ represents a phenyl group, naphthyl group or thienyl group which group R$^2$ may optionally be substituted by one or more halogen atoms, methyl groups, methoxy groups, cyclopentoxy groups, nitro groups or dimethyl amino groups.
4. A compound according to claim 3 wherein R$^2$ represents a phenyl, 3-chlorophenyl, 4-chlorophenyl, 3-fluorophenyl, 4-fluorophenyl or 3-nitrophenyl group.

5. A compound according to claim 1 or 2 wherein $R^3$ represents a hydrogen atom, a $C_{1-6}$ alkyl group or a chlorine atom at the 8- or 9-position of the 1,2,4triazolo[4,3-b]pyrido[3,2-d]pyridazine skeleton.

6. A compound according to claim 1 which is 6-(4-fluorophenyl)-3-isobutyl-1,2,4-triazolo[4,3-b]pyrido[3,2-d]pyridazine, 3-cyclopropylmethyl-6-(3-nitrophenyl)-1,2,4-triazolo [4, 3-b] pyrido [3, 2-d]pyridazine, 3-cyclopropyl-6-phenyl-1,2,4-triazolo[4,3-b]pyrido[3,2-d]pyridazine and 3-cyclobutylmethyl-6-(3-nitrophenyl)-1,2,4-triazolo[4,3-b]pyrido[3,2d]pyridazine.

7. A composition comprising a compound according to claim 1 or 2 or a pharmaceutically acceptable salt thereof mixed with a pharmaceutically acceptable diluent or carrier.

8. A process for preparing a compound of formula (I)

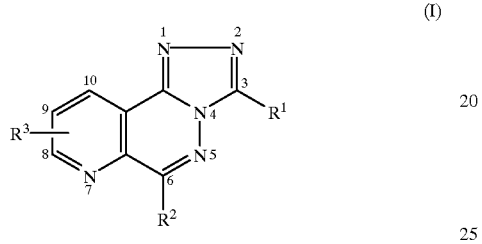

(I)

wherein;

$R^1$ represents a hydrogen atom or a —$(CH_2)_m$ Y group, wherein m is an integer from 0 to 4 and Y represents a $C_1$–$C_6$ alkyl, $C_1$–$C_6$ haloalkyl, $C_1$–$C_6$ alkoxy, $C_2$–$C_7$ alkoxycarbonyl, $C_3$–$C_7$ cycloalkyl, norbornyl or $C_8$–$C_{12}$ phenylalkenyl group, or a phenyl or pyridyl group which may be unsubstituted or substituted by one or more halogen atoms;

$R^2$ represents a phenyl, naphthyl or thienyl group which may be unsubstituted or substituted by one or more halogen atoms or $C_1$–$C_6$ alkyl, $C_1$–$C_6$ alkoxy, $C_3$–$C_6$ cycloalkoxy, methylenedioxy, nitro, di($C_1$–$C_6$) alkylamino or trifluoromethyl groups; and $R^3$ represents a hydrogen or halogen atom or a C1–C6 alkyl group, which process comprises formation of the 1,2,4-triazole ring present in formula (I) by cyclisation of a hydrazide of formula (IV)

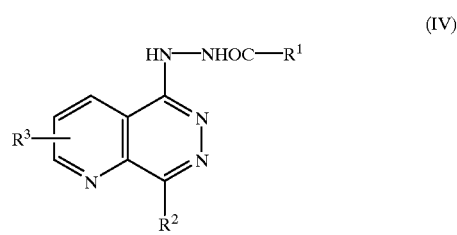

(IV)

wherein $R^1$ $R^2$ and $R^3$ are as defined above.

* * * * *